(12) United States Patent
Sakamoto

(10) Patent No.: US 9,186,308 B2
(45) Date of Patent: Nov. 17, 2015

(54) COMPOSITION FOR ORAL CAVITY

(71) Applicant: SUNSTAR, INC., Takatsuki-shi, Osaka (JP)

(72) Inventor: Hiroshi Sakamoto, Takatsuki (JP)

(73) Assignee: SUNSTAR INC., Osaka (JP)

(*) Notice: Subject to any disclaimer, the term of this patent is extended or adjusted under 35 U.S.C. 154(b) by 0 days.

(21) Appl. No.: 14/211,545

(22) Filed: Mar. 14, 2014

(65) Prior Publication Data

US 2014/0199355 A1 Jul. 17, 2014

Related U.S. Application Data

(63) Continuation of application No. 13/501,512, filed as application No. PCT/JP2010/068070 on Oct. 14, 2010, now Pat. No. 8,734,764.

(30) Foreign Application Priority Data

Oct. 14, 2009 (JP) ................................. 2009-237785
Apr. 23, 2010 (JP) ................................. 2010-099954

(51) Int. Cl.
*A61K 8/02* (2006.01)
*A61K 8/25* (2006.01)
*A61Q 11/00* (2006.01)

(52) U.S. Cl.
CPC ................ *A61K 8/25* (2013.01); *A61K 8/0241* (2013.01); *A61Q 11/00* (2013.01); *A61K 2800/412* (2013.01)

(58) Field of Classification Search
CPC .................................................. A61K 8/0241
See application file for complete search history.

(56) References Cited

U.S. PATENT DOCUMENTS

| | | | |
|---|---|---|---|
| 5,004,488 A | 4/1991 | Mehrotra et al. | |
| 5,071,638 A | 12/1991 | Yoshie et al. | |
| 5,512,271 A | 4/1996 | McKeown et al. | |
| 5,676,932 A | 10/1997 | Wason et al. | |
| 6,290,933 B1 | 9/2001 | Durga et al. | |
| 8,221,723 B2 | 7/2012 | Deckner et al. | |
| 2010/0135934 A1 | 6/2010 | Deckner et al. | |

FOREIGN PATENT DOCUMENTS

| | | |
|---|---|---|
| JP | S5590555 A | 7/1980 |
| JP | 62-241541 A | 10/1987 |
| JP | 63-162617 A | 7/1988 |
| JP | 05-208808 A | 8/1993 |
| JP | 10-139644 A | 5/1998 |
| JP | 10-511684 A | 11/1998 |
| JP | 11-130655 A | 5/1999 |
| JP | 2001-003034 A | 1/2001 |
| JP | 2004-238321 A | 8/2004 |
| JP | 2009-001638 A | 1/2009 |
| WO | WO 2010/068471 A2 | 6/2010 |

OTHER PUBLICATIONS

International Search Report mailed on Jan. 25, 2011 for the corresponding International patent application No. PCT/JP2010/068070.
"A.3.6. Reference abrasive slurry" International Standard ISO 11609, p. 5, 1995.
John J. Hefferren, "A Laboratory Method for Assessment of Dentifrice Abrasivity," *J. Dent. Res.*, vol. 55, No. 4, pp. 563-573, 1976.
Stookey et al., "In vitro Removal of Stain with Dentifrices," *J. Dent. Res.*, vol. 61, No. 11, pp. 1236-1239, 1982.

*Primary Examiner* — Benjamin Packard
(74) *Attorney, Agent, or Firm* — Posz Law Group, PLC

(57) ABSTRACT

An oral composition includes high stain removal efficiency relative to its abrasive ability. The oral composition contains fused silica and a dental abrasive. The oral composition has a high stain removal ability relative to the abrasive ability thereof. In other words, the ratio (stain removal ability/abrasive ability) of the oral composition is high. Accordingly, the use of the oral composition makes it possible to efficiently remove stains without damaging the teeth more than necessary.

20 Claims, No Drawings

COMPOSITION FOR ORAL CAVITY

CROSS REFERENCE TO RELATED APPLICATIONS

This application is a continuation application of U.S. application Ser. No. 13/501,512 filed Jun. 14, 2012 which is a U.S. national stage application of PCT/JP2010/068070 filed on Oct. 14, 2010, and claims priority to, and incorporates by reference, Japanese Patent Application No. 2009-237785 filed on Oct. 14, 2009 and No. 2010-099954 filed on Apr. 23, 2010.

TECHNICAL FIELD

The present invention relates to an oral composition. More specifically, the present invention relates to an oral composition comprising fused silica and a dental abrasive.

BACKGROUND

Teeth discoloration results from deposition of chromogenic substances called stains on the teeth, and this causes a serious problem in terms of aesthetic appreciation. As a means to remove stains, a common method is such that an oral composition such as a dentifrice composition containing a dental abrasive is held in the mouth using a tool such as a toothbrush, and the teeth are brushed. Because stains are removed mainly by abrasion, it is believed that a higher stain removal effect is achieved by the use of a dental abrasive having a higher abrasive ability. From this viewpoint, a harder dental abrasive would be preferable for the removal of stains, because a harder dental abrasive is considered to abrade the tooth surface with more physical strength and provide a high stain removal effect.

However, when an oral composition containing a dental abrasive having a high abrasive ability is used, there is a risk that the teeth may be abraded more than necessary. When the tooth surface is abraded, the dentine may be exposed, which may cause hypersensitivity. Further, because the exposed dentine has poor resistance to acid, tooth decay may be promoted. For example, alumina, i.e., a typical example of a hard dental abrasive, has an excellent stain removal ability, but also damages the teeth by abrasion. Although various improvements have been made to prevent damage to the teeth, the problem has not yet been solved. Today, oral compositions rarely contain alumina.

Therefore, there is a demand for the development of an oral composition having a high stain removal ability while having an appropriate abrasive ability; specifically, an oral composition having a high stain removal ability relative to its abrasive ability (i.e., the balance between the abrasive ability and the stain removal ability is good).

For example, Patent Literature 1 discloses that an oral composition comprising two types of silica having different abrasivities (silica with high abrasivity and silica with low abrasivity) as dental abrasives is useful to remove stains without damaging the teeth. However, this oral composition also contains highly abrasive silica, and thus has not exactly eliminated the risk of damaging the teeth.

CITATION LIST

Patent Literature

PTL 1: Japanese Unexamined Patent Publication No. 2004-238321
PTL 2: Japanese Unexamined Patent Publication No. 2009-1638
PTL 3: Japanese Unexamined Patent Publication No. 562-241541

SUMMARY

An object of the present invention is to provide an oral composition whose stain removal efficiency is high relative to its abrasive ability.

The present inventors unexpectedly found that an oral composition containing fused silica has a high stain removal ability, even though its abrasive ability is not particularly high; i.e., the stain removal ability is high relative to the abrasive ability. Further, the present inventors found that when an oral composition contains fused silica and a dental abrasive, the stain removal ability is even higher relative to the abrasive ability. The present inventors completed the present invention with further improvements based on the above findings.

Fused silica is a type of silica used in the field of semiconductors, and is mainly used as a filler and the like, for example, in thermosetting resin for semiconductor sealant (for example, see Japanese Unexamined Patent Publication No. 2009-1638). However, an oral composition containing fused silica is not known. Further, because fused silica is produced by fusing silica powder at high temperatures, the density is high, and the hardness is very high. As described above, a harder dental abrasive has a higher abrasive ability, and such a dental abrasive may abrade the teeth more than necessary. Therefore, it was completely unexpected that an oral composition containing fused silica having a very high hardness would have a high stain removal ability despite its not very high abrasive ability.

Specifically, the present invention encompasses oral compositions recited in the following items, for example.
Item 1.
An oral composition comprising fused silica and a dental abrasive.
Item 2-1.
The oral composition according to Item 1, comprising 0.25 to 8.5% by mass of the fused silica.
Item 2-2.
The oral composition according to Item 1, comprising 0.5 to 8.5% by mass of the fused silica.
Item 3-1.
The oral composition according to any one of Items 1 to 2-2, wherein the BET specific surface area of the fused silica is 10 ($m^2/g$) or less.
Item 3-2.
The oral composition according to any one of Items 1 to 3-1, wherein the BET specific surface area of the dental abrasive is 20 to 1,000 ($m^2/g$).
Item 4-1.
The oral composition according to any one of Items 1 to 3-2, wherein the fused silica has an oil absorption of 20 (mL/100 g) or less.
Item 4-2.
The oral composition according to any one of Items 1 to 4-1, wherein the dental abrasive has an oil absorption of 20 to 400 (mL/100 g).

Item 5.
The oral composition according to any one of Items 1 to 4, wherein the dental abrasive is at least one member selected from the group consisting of precipitated silica, silica gel, fumed silica, zircono-silicate, aluminum silicate, calcium phosphate, anhydrous dicalcium phosphate, dicalcium phosphate dihydrate, tricalcium phosphate, anhydrous calcium hydrogen phosphate, calcium hydrogen phosphate dihydrate, calcium pyrophosphate, calcium carbonate, calcium sulfate, aluminum hydroxide, water-insoluble sodium metaphosphate, trimagnesium phosphate, magnesium carbonate, titanium oxide, polymethylmethacrylate, bentonite, hydroxyapatite, crystalline cellulose, polyethylene beads, and polypropylene beads.
Item 6.
The oral composition according to Item 5, wherein the dental abrasive is precipitated silica.
Item 7.
The oral composition according to Item 6, comprising 5 to 26% by mass, preferably 7.5 to 26% by mass, of the precipitated silica.
Item 8.
The oral composition according to Item 6 or 7, comprising a total of 10 to 34.5% by mass of the fused silica and the precipitated silica.
Item 9.
The oral composition according to any one of Items 6 to 8, wherein the mass ratio of the precipitated silica to the fused silica (precipitated silica/fused silica) contained in the oral composition is 2.5-11:1.
Item 10-1.
The oral composition according to any one of Items 1 to 9 for use in the cleaning of the teeth.
Item 10-2.
The oral composition according to any one of Items 1 to 9 for the use in the removal of stains attached to the teeth.
Item 11.
The oral composition according to any one of Items 1 to 10-2, wherein the fused silica is fused silica in which particles having a particle size greater than 60 µm are substantially removed.
Item 12.
The oral composition according to any one of Items 1 to 11, wherein the fused silica is fused silica sieved through a 60-µm mesh.
Item 13.
The oral composition according to any one of Items 1 to 12, wherein the RDA value is 90 to 140.
Item 14.
The oral composition according to any one of Items 1 to 13, comprising fused silica having different average particle sizes.
Item 15.
The oral composition according to Item 14, comprising fused silica having an average particle size of 0.1 to 10 µm and fused silica having an average particle size greater than 10 µm and is equal to or less than 45 µm.
Item 16.
The oral composition according to Item 14 or 15, wherein the mass of the fused silica having an average particle size of 0.1 to 10 µm accounts for 10 to 90% of the total mass of the fused silica.
Item 17.
The oral composition according to any one of Items 1 to 16, wherein the dental abrasive has an RDA value of 20 to 200.

Item 18.
The oral composition according to any one of Items 1 to 17, wherein the degree of roundness of fused silica particles is 0.89 or more.
Further, the present invention also encompasses stain removal methods recited in the following items, for example.
Item A-1.
A method for removing stains from a tooth with stains attached, comprising the step of applying the oral composition recited in any one of Items 1 to 13 in the oral cavity.
Item A-2.
A method for removing stains from a tooth with stains attached, comprising the step of brushing the teeth using the oral composition recited in any one of Items 1 to 13.

The oral composition of the present invention has a high stain removal ability and a low abrasive ability. Therefore, the risk of damaging the teeth by abrasion is low. Accordingly, the use of the oral composition of the present invention makes it possible to remove stains in a highly efficient manner, practically without damaging the teeth.

DETAILED DESCRIPTION

The present invention is described in more detail below.
The oral composition of the present invention comprises fused silica and a dental abrasive, and is used as a composition for cleaning the teeth. In particular, stains can be removed in a highly efficient manner, for example, by brushing the teeth using the oral composition of the present invention. Further, when doing so, the problem of damage to the teeth by abrasion is very unlikely to occur.

As described above, fused silica is used in the field of semiconductors, and is either known or can be produced by a known method. Such fused silica can be used in the present invention. Fused silica can be obtained by, for example, fusing silicon dioxide powder as a raw material (for example, silica powder) by flames at high temperatures (for example, 2,000 to 3,000° C.). Further, fused silica can also be obtained, for example, by oxidizing and dissolving silicon powder or cyclic siloxane by high-temperature flames. In this way, because fused silica is produced by a high-temperature treatment, the risk of contamination is low. Additionally, because silica is fused once and solidified, silica particles have a high density and an increased hardness. In particular, "thermally sprayed and fused silica (fused silica obtained by thermal spraying)", which is obtained from crushed silica powder as a raw material using a burner that sprays flames at high temperatures and by the application of a thermal spraying technique, can be preferably used as fused silica to be contained in the oral composition of the present invention. In particular, because the thermally sprayed and fused silica is obtained as a solid after most of the particles are fused, the hardness and the degree of sphericity are high. Therefore, as described below, the thermally sprayed and fused silica is particularly preferable as fused silica to be contained in the oral composition of the present invention. Although not particularly limited, such thermally sprayed and fused silica can be preferably produced, for example, by a method disclosed in Japanese Unexamined Patent Publication No. S62-241541.

Silica particles of the fused silica contained in the oral composition of the present invention preferably have a high degree of sphericity (the shape is close to a complete sphere). The degree of sphericity can be evaluated by "the degree of roundness," which indicates how close the contour of the globe is to a true circle. The degree of roundness can be calculated as follows: (i) first, an image of the target particle for the measurement of the degree of roundness is taken, and the contour of the particle is traced to calculate the contour length and the area; and (ii) next, a circle having the same area as that of the contour of the particle whose image was taken is drawn, and the circumferential length of the circle is calculated. At this time, the degree of roundness can be determined by the following formula. The degree of roundness is 1 when the contour of a particle is a true circle, and the degree of roundness is never greater than 1.

$$\text{Degree of roundness} = \frac{\text{circumferential length calculated in (ii)}}{\text{contour length or the particle calculated in (i)}}$$

The degree of roundness can be measured using a roundness measuring instrument (JIS B7451: 1997). A preferable instrument is one that disperses particles in a liquid such as water, allows the particles to pass through the flow cell so as to take an image of the particles, and performs analysis in a real-time manner. A particle image analyzer (FPIA-3000 by Sysmex Corporation) can be preferably used.

Fused silica particles contained in the oral composition of the present invention preferably have a degree of roundness of 0.89 or more, more preferably 0.93 or more, and still more preferably 0.95 or more.

Further, the fused silica has a smaller BET specific surface area compared to known dental abrasives (for example, wet silica such as precipitated silica and silica gel). The fused silica contained in the oral composition of the present invention usually has a BET specific surface area ($m^2/g$) of 15 or less, preferably 10 or less, more preferably 8 or less, and still more preferably 5 or less. The BET specific surface area of silica can be measured using a Macsorb HM model-1201 (Mountech Co., Ltd.).

Further, the fused silica contained in the oral composition of the present invention preferably has a low oil absorption (linseed oil absorption; JIS K5101). Specifically, the fused silica usually has an oil absorption (mL/100 g) of 20 or less, preferably 10 or less, more preferably 8 or less, and still more preferably 5 or less.

It is believed that when fused silica has a smaller BET specific surface area, silica particles of the fused silica have a higher density and an increased hardness. It is also believed that when fused silica has a lower oil absorption, silica particles of the fused silica have a higher density and an increased hardness. Specifically, it is believed that the smaller the BET specific surface area and the lower the oil absorption of the fused silica, the higher the hardness of silica particles of the fused silica.

Commercially available fused silica may be purchased and used as the fused silica contained in the oral composition of the present invention. Purchases can be made from, for example, Denki Kagaku Kogyo Kabushiki Kaisha (commercially available as Denka fused silica (FB, FBX)), Micron Inc. (commercially available as spherical silica), and the like.

When fused silica having a high hardness is added to the oral composition and applied in the oral cavity, it may leave a gritty sensation in the oral cavity of the user. Such a sensation may not be a problem to some users, but may undesirably provide an uncomfortable sensation to other users, as if stones or sand is inside their oral cavities; therefore, it is desirable to minimize such an uncomfortable sensation.

Such an uncomfortable sensation can be reduced by, for example, reducing the amount of fused silica contained in the oral composition, and reducing the particle size of silica particles of the fused silica contained in the oral composition.

Accordingly, although it is not particularly limited, silica particles having a relatively large particle size are preferably removed from the fused silica contained in the oral composition of the present invention. The removal can be performed by, for example, passing the particles through a mesh.

Specifically, fused silica in which particles having a particle size greater than 60 µm are substantially removed is preferable. Fused silica in which particles having a particle size greater than 55 µm are substantially removed is more preferable. Herein, the phrase "substantially removed" does not mean that such particles are not contained at all, but that a removal procedure is performed by, for example, using a mesh or the like, so that such particles are substantially not contained.

In other words, the particle size of particles of the fused silica contained in the oral composition of the present invention is preferably 60 µm or less, and more preferably 55 µm or less. This also means performing a removal procedure by, for example, using a mesh or the like having a specific sieve size so that silica substantially has a specific particle size or less. For example, fused silica comprising particles of a particle size of 53 µm or less can be obtained by using a 53-µm mesh. Substantially, the particle size of the fused silica contained in the oral composition of the present invention is preferably 60 µm or less (more preferably 55 µm or less, still more preferably 53 µm or less, and still yet more preferably 45 µm or less).

Specifically, the fused silica contained in the oral composition of the present invention is fused silica preferably sieved through a 60-µm mesh, more preferably a 55-µm mesh, still more preferably a 53-µm mesh, and still yet more preferably a 45-µm mesh. For example, such fused silica can be obtained by sieving commercially available fused silica through a specific-size mesh. Further, some of the commercially available fused silica has been already sieved, and such fused silica can also be preferably used in the present invention.

Additionally, the fused silica contained in the oral composition of the present invention preferably has an average particle size (50% cumulative diameter; d50) of about 0.1 to about 45 µm, more preferably about 1 to about 20 µm, and still more preferably about 3 to about 17 µm. Preferably, the fused silica obtained by removing silica particles having a large particle size has an average particle size (d50) in the above-mentioned range.

The average particle size (d50) of the fused silica is a value determined using water as a dispersion medium by a laser diffraction scattering measuring device. It can be measured by LA-920 (Horiba, Ltd.).

Further, the fused silica contained in the oral composition of the present invention has preferably a relative dentine abrasivity (RDA) value of 60 to 160 and more preferably 80 to 140. The RDA of the fused silica is the measurement obtained by preparing a slurry of fused silica by the method described in "A. 3.6 Standard Abrasive Slurry" by ISO11609: 1995, and by measuring the slurry by the method of Hefferen et al. (J. Dent. Res., Vol. 55, No. 4, 563-573, 1976).

Additionally, it is particularly preferable that different types of fused silica having different average particle sizes are used in combination in the production of the oral composition of the present invention. Specifically, the fused silica contained in the oral composition of the present invention preferably comprises a mixture of two (or more) types of fused silica having different average particle sizes. When two (or more) types of fused silica having different average particle sizes are used in combination, it is possible to obtain an oral composition in which the stain removal ability is further enhanced, and the stain removal ability is high relative to the abrasive ability.

For example, when two types of fused silica having different average particle sizes are used in combination, and when one having a smaller average particle size is referred to as fine fused silica and the other one having a greater average particle size is referred to as coarse fused silica, the average particle size of the fine fused silica is preferably 0.1 to 10 μm, more preferably 0.1 to 6 μm, and still more preferably 0.2 to 3 μm, and the average particle size of the coarse fused silica is preferably greater than 10 μm and not greater than 45 μm, more preferably 12 to 30 μm, and still more preferably 15 to 20 μm. Further, in this case, the content percentage of the fine fused silica is preferably 10 to 90% and more preferably 30 to 90% (or 30 to 80%), when the percentage of the total fused silica is assumed to be 100%.

The dental abrasive added to the oral composition of the present invention is a known dental abrasive. Examples of such dental abrasives include precipitated silica (in particular, abrasive precipitated silica), silica gel, fumed silica, zirconosilicate, aluminum silicate, calcium phosphate, anhydrous dicalcium phosphate, dicalcium phosphate dihydrate, tricalcium phosphate, anhydrous calcium hydrogen phosphate, calcium hydrogen phosphate dihydrate, calcium pyrophosphate, calcium carbonate, calcium sulfate, aluminum hydroxide, water-insoluble sodium metaphosphate, trimagnesium phosphate, magnesium carbonate, titanium oxide, polymethylmethacrylate, bentonite, hydroxyapatite, crystalline cellulose, synthetic resins (for example, polyethylene beads and polypropylene beads), and the like. Of these, precipitated silica is particularly preferable. Further, these dental abrasives can be used singly, or in a combination of two or more thereof.

These known dental abrasives have a larger BET specific surface area compared to fused silica. The dental abrasive added to the oral composition of the present invention usually has a BET specific surface area ($m^2/g$) of 20 to 1,000, preferably 20 to 400. Further, known dental abrasives often have a higher oil absorption (linseed oil absorption, JIS K5101), compared to fused silica. The dental abrasive added to the oral composition of the present invention usually has an oil absorption (mL/100 g) of 20 to 400. Further, the dental abrasive added to the oral composition of the present invention preferably has a relative dentine abrasivity (RDA) value of 20 to 200. The RDA of the dental abrasive is the measurement obtained by preparing a slurry of fused silica by the method described in "A. 3.6 Standard Abrasive Slurry" by ISO11609: 1995, and by measuring the slurry by the method of Hefferen et al. (J. Dent. Res., Vol. 55, No. 4, 563-573, 1976).

The oral composition of the present invention preferably contains 0.25 to 8.5% by mass of fused silica, more preferably 0.5 to 8.5% by mass, still more preferably 2 to 5% by mass, and still yet more preferably 3 to 4.5% by mass, relative to the total composition. When the fused silica is contained in the above ranges, it is preferable not only from the viewpoint of the balance between the abrasive ability and the stain removal ability, but also from the viewpoint of low risk of providing the users the above-described uncomfortable sensation, as if stones or sand is inside their oral cavities, when they use the fused silica.

Further, the amount of the dental abrasive added to the oral composition of the present invention can be suitably set according to the type of the dental abrasive. For example, preferably 2 to 70% by mass, more preferably 5 to 60% by mass, of the dental abrasive is contained in the total composition. In particular, when precipitated silica is used as the dental abrasive, the precipitated silica is contained in an amount of preferably 5 to 26% by mass, more preferably 7.5 to 26% by mass, still more preferably 7.5 to 22% by mass, still yet more preferably 15 to 22% by mass, and particularly preferably 17 to 22% by mass, relative to the total composition.

Further, when precipitated silica is used as the dental abrasive, precipitated silica and fused silica are preferably contained in a total amount (i.e., the total content) of 10 to 34.5% by mass, more preferably 15 to 34.5% by mass, relative to the total composition. Still further, when precipitated silica is used as the dental abrasive, the mass ratio of the precipitated silica to the fused silica (precipitated silica/fused silica) is preferably 2.5-11:1, preferably 3-11:1, and more preferably 4-8:1.

The oral composition of the present invention containing the fused silica and the dental abrasive in the above ranges has, in particular, a high stain removal ability, although the abrasive ability thereof is low. Therefore, the use of the oral composition makes it possible to highly efficiently remove stains without abrading the teeth more than necessary.

The oral composition of the present invention containing the fused silica and the dental abrasive can be produced by a known method that is usually used to produce an oral composition.

Still further, the oral composition of the present invention can be used for the teeth or dentures, and can be formed into a dentifrice in any of the following forms by a common method: paste, powder, cream, gel, liquid, and the like. In particular, a dentifrice in the form of a paste, powder, cream, or gel is preferable.

The oral composition of the present invention can be produced by mixing, for example, a pharmaceutically or dental-hygienically accepted substance, fused silica, and a dental abrasive (and other components, if necessary). Examples of such substances include water, glycerol, ethylene glycol, diethylene glycol, polyethylene glycol, propylene glycol, polypropylene glycol, sorbitol, xylitol, lactitol, mannitol, ethanol, and the like.

The oral composition of the present invention may contain other components (optional components) that are usually added to oral compositions.

For example, a non-ionic surfactant, an anionic surfactant, or a zwitterionic surfactant may be added as a surfactant. Specifically, examples of non-ionic surfactants include fatty acid ester, fatty acid alkanolamides, sorbitan fatty acid ester, fatty acid monoglyceride, polyglycerol fatty acid ester, polyoxyethylene alkyl phenyl ether, alkyl glycoside, diethyl sebacate, polyoxyethylene hydrogenated castor oil, polyoxyethylene sorbitan fatty acid ester, and the like. Examples of anionic surfactants include alkyl sulfate salt, polyoxyethylene alkyl ether sulfate salt, alkyl sulfosuccinate, polyoxyethylene alkyl ether sulfosuccinate, N-acylamino acid salt, N-acyltaurine salt, alkyl ether carboxylate, alkyl phosphate, polyoxyethylene alkyl ether phosphate, fatty acid monoglyceride sulfate, alkyl sulfoacetate, and the like. Examples of zwitterionic surfactants include alkyl dimethyl aminoacetate betaine, alkyl amidopropyldimethyl aminoacetate betaine, N-acyl-N-carboxymethyl-N-hydroxyethylethylenediamine, N-alkylaminoethylglycine, and the like. These surfactants can be added singly, or in a combination of two or more thereof. The amount to be added is usually 0.1 to 10% by mass relative to the total mass of the composition.

Examples of thickeners that can be added include cellulose derivatives such as carrageenan, carboxymethyl cellulose, hydroxypropyl cellulose, hydroxypropyl methyl cellulose, and hydroxyethyl cellulose; gums such as xanthan gum, tragacanth gum, karaya gum, gum arabic, and gellan gum; synthetic binders such as polyvinyl alcohol, sodium polyacrylate, carboxy vinyl polymer, and polyvinylpyrrolidone; inorganic binders such as thickening silica, aluminum silica gel, and veegum; sodium alginate; pectin; soybean polysaccharides; sodium chondroitin sulfate; sodium hyaluronate; and the like. These thickeners can be added singly, or in a combination of two or more thereof. The thickener is usually added in an amount of 0.01 to 20% by mass.

Examples of flavoring agents that can be added include menthol, carboxylic acid, anethole, eugenol, methyl salicylate, limonene, ocimene, n-decyl alcohol, citronellal, α-terpineol, methyl acetate, citronellyl acetate, methyleugenol, cineol, linalool, ethyl linalool, thymol, spearmint oil, peppermint oil, lemon oil, orange oil, sage oil, rosemary oil, cinnamon oil, beefsteak plant oil, wintergreen oil, clove oil, eucalyptus oil, pimento oil, d-camphor, d-borneol, fennel oil, cinnamon oil, cinnamaldehyde, mint oil, vanillin, and the like. These flavoring agents can be added singly, or in a combination of two or more thereof, usually in an amount of 0.01 to 1% by mass relative to the total mass of the composition.

Further, sweetening agents such as sodium saccharin, acesulfame potassium, stevioside, neohesperidyl dihydrochalcone, glycyrrhizin, perillartine, thaumatin, asparatyl phenylalanyl methyl ester, and p-methoxycinnamic aldehyde can be added singly, or in a combination of two or more thereof; usually in an amount of 0.01 to 1% by mass relative to the total mass of the composition.

Further, wetting agents such as sorbit, ethylene glycol, propylene glycol, glycerol, 1,3-butylene glycol, polypropylene glycol, xylitol, maltitol, lactitol, Palatinit, and polyethylene glycol can be added singly, or in a combination of two or more thereof.

The oral composition of the present invention may contain an active ingredient. Examples thereof include cationic disinfectants such as cetylpyridinium chloride, benzalkonium chloride, benzethonium chloride, and chlorhexidine hydrochloride; vitamin E such as dl-α-tocopherol acetate, tocopherol succinate, and tocopherol nicotinate; amphoteric disinfectants such as dodecyldiaminoethylglycine; non-ionic disinfectants such as triclosan and isopropylmethylphenol; enzymes such as dextranase, amylase, protease, mutanase, lysozyme, and lytic enzyme; fluorides such as sodium monofluorophosphate, sodium fluoride, and stannous fluoride; tranexamic acid; epsilon aminocaproic acid; aluminum chlorohydroxy allantoin; dihydrocholesterol; glycyrrhetinic acid; glycerophosphate; chlorophyll; sodium chloride; calpeptide; dipotassium glycyrrhizinate; allantoin; hinokitiol; potassium nitrate; and the like. These components may be added singly, or in a combination of two or more thereof.

Further, any container can be used to place the oral composition of the present invention therein without specific limitation. For example, a container made of glass, metal, plastic, a laminator material, or the like may be used. Further, the shape of the container is also not particularly limited. For example, a container such as a bottle, a cup, a pouch, or a tube can be used.

As described above, the oral composition of the present invention can highly efficiently remove stains, even though the abrasive ability thereof is not particularly high. The abrasive ability can be specifically indicated by the relative dentine abrasivity (RDA) value. The abrasive ability (RDA value) of the oral composition of the present invention is preferably 200 or less, and more preferably 150 or less. In particular, the RDA value is preferably 90 to 140, and more preferably 100 to 140. The RDA value is a value that indicates the degree of abrasivity on dentine, and can be determined by the method of Hefferen et al. (J. Dent. Res., Vol. 55, No. 4, 563-573, 1976).

Further, the stain removal ability of the oral composition of the present invention can be determined by a modified method of the method of Stooky et al. (J. Dent. Res., Vol. 61, No. 11, 1236-1239, 1982). Specifically, the stain removal ability can be measured by evaluating the color of the tooth surface using the L*a*b* color system as follows: when L*, a*, and b* values (respectively, L0, a0, and b0) of the tooth surface before staining, L*, a*, and b* values (respectively, L1, a1, and b1) of the tooth surface after staining, and L*, a*, and b* values (respectively, L2, a2, and b2) of the tooth surface after stain removal are measured, the stain removal ability (ΔE) can be calculated by the following formula.

$$\text{Stain removal ability}(\Delta E)=100\times(\Delta E1/\Delta E0),$$

wherein $$\Delta E1=\sqrt{(L2-L1)^2+(a2-a1)^2+(b2-b1)^2}$$

$$\Delta E0=\sqrt{(L2-L0)^2+(a2-a0)^2+(b2-b0)^2}$$

The L*, and b* values can be measured using a colorimeter. A bovine enamel tooth fragment, for example, can be used as the tooth for measurement. Additionally, it is preferable to mirror-polish the surface of the tooth fragment prior to measuring the tooth surface before being discolored with stains. The L* value (i.e., L1) of the tooth surface after being discolored with stains is preferably 30 or less. When removing stains using an oral composition, it is preferable to soak the tooth fragment in the composition or its diluted solution (for example, 2-fold or 3-fold dilution), and to brush (for example, an arbitrary value in the range of 100 to 2,000 strokes, preferably in the range of 500 to 1,500 strokes, is set to brush the tooth surface). Brushing is performed using a BSI-standard brushing machine equipped with a regular toothbrush.

More specifically, the stain removal ability can be measured by a method described in the Examples.

The stain removal ability of the oral composition of the present invention, which can be measured as described, is preferably 25 or higher, and more preferably 27 or higher.

The L*a*b* color system is a color system commonly used to describe the color of an object. The L*a*b* color system was standardized by the International Commission on Illumination (CIE) in 1976, and has been incorporated into JIS (JIS 28729) in Japan.

The ratio of the stain removal ability to the abrasive ability (stain removal ability/abrasive ability) of the oral composition of the present invention is about 0.2 or greater, more preferably about 0.23 or greater, and still more preferably 0.25 or greater.

The oral composition of the present invention is applicable not only to humans, but also other animals (in particular, mammals) that have teeth. Examples of such animals include pets and farm animals, specifically, dogs, cats, monkeys, cows, horses, pigs, sheep, hamsters, rabbits, and the like.

The present invention also encompasses a method for applying the above-described oral composition in the oral cavity to remove stains on the tooth. A method for applying the oral composition in the oral cavity can be suitably selected according to the form of the oral composition, dosage form, and the like. For example, when the oral composition is a liquid (for example, a liquid tooth paste, a mouthwash, or the like), examples of methods include placing the oral composition in the oral cavity and rinsing the mouth. There is another example, for example, in which an appropriate amount of the oral composition (in particular, in the solid or paste form) is placed on a toothbrush, and the teeth are brushed. Stains on detached dentures can also be removed by the above methods. Further, the target of these methods is as described above, and it is not particularly limited to humans.

Examples

The present invention is described in detail below, but the present invention is not limited to the examples described below.

<Examination of Abrasive Ability and Stain Removal Ability>

Preparation of Oral Composition

An oral composition containing fused silica and a dental abrasive was produced as described below. Below, precipitated silica was used as a dental abrasive.

<Silica>

The following fused silica and precipitated silica were used as silica to be contained in the oral composition. Fused silica sieved through a 53-μm mesh was used. Fused Silica (purchased from Micron Inc.)
  BET specific surface area: 3.5 (m$^2$/g)
  Oil absorption (linseed oil absorption, JIS K5101): 5 (mL/100 g)
  Degree of roundness: 0.95
  Average particle size (d50): 14 μm
  RDA: 130

Precipitated silica (purchased from Nihon Silica Kogyo, Ltd.)
  BET specific surface area: 104 (m$^2$/g)
  Oil absorption (linseed oil absorption, JIS K5101): 110 (mL/100 g)
  Degree of roundness: 0.69
  Average particle size (d50): 12 μm
  RDA: 100

These fused silica and precipitated silica were mixed with the components described in Table 1, and the amount of silica contained was changed, thereby producing an oral composition (paste-like dentifrice) of each example (Tables 2 to 4).

TABLE 1

| Components | Amount (mass %) |
| --- | --- |
| Precipitated silica | Shown in Tables 2 to 5 |
| Fused Silica | Shown in Tables 2 to 5 |
| Sorbitol | 35 |
| Glycerol | 13 |
| Sodium lauryl sulfate | 5 |
| Disodium polyoxyethylene (2 mol) alkyl (C12-14) sulfosuccinate | 5 |
| polyoxyethylene hydrogenated castor oil | 1 |
| Sodium carboxymethyl cellulose | 1 |
| Sodium alginate | 1 |
| Purified water | Balance |
| Total | 100 |

The stain removal ability and the abrasive ability of the thus-obtained oral composition of each example were examined in the following manner.

<Stain Removal Ability>

The stain removal ability (ΔE) was measured by a modified method of the method of Stooky et al. (J. Dent. Res., Vol. 61, No. 11, 1236-1239, 1982) and calculated. Specifically, the measurement and calculation were carried out as follows using the L*a*b* color system.

A bovine enamel tooth fragment was cut out and embedded in transparent polyester resin, and the surface of the tooth fragment was mirror-polished. After washing with ion-exchange water, the tooth fragment was fully dried, and L*, a*, and b* values were measured using a colorimeter (CR-241 produced by Konica Minolta Sensing, Inc.). The thus-obtained values were determined to be L0, a0, and b0, respectively. Further, the surface of the tooth fragment was etched by sequentially using 0.2 M of hydrochloric acid, saturated sodium carbonate aqueous solution, and 1% phytic acid aqueous solution; and then placed on a stain application machine. Stains were applied for 7 days using an aqueous solution of a mixture of tea, coffee, and mucin from porcine stomach as a staining medium. On day 8 and onward, discoloration of the tooth fragment was continued until the L* value was 30 or below, by adding ferric chloride to the staining medium. After staining was finished, L*, a*, and b* values were measured using the colorimeter. The values were determined to be L1, a1, and b1, respectively. The stained tooth fragment was set in a BSI-standard brushing machine equipped with a regular toothbrush. The tooth fragment was brushed for 1,000 strokes in a 3-fold dilution of the oral composition of each of the Examples and Comparative Examples. Subsequently, L*, a*, and b* values were measured using the colorimeter. The values were determined to be L2, a2, and b2, respectively. Then, a value expressed by the following formula was calculated as the stain removal ability (ΔE) (rounded off to the nearest whole number), and evaluated.

Stain removal ability(ΔE)=100×(ΔE1/ΔE0), wherein $$\Delta E1 = \sqrt{(L2-L1)^2 + (a2-a1)^2 + (b2-b1)^2}$$

$$\Delta E0 = \sqrt{(L2-L0)^2 + (a2-a0)^2 + (b2-b0)^2}$$

The staining medium used herein and elsewhere was prepared by putting 4 commercially available tea bags into about 1,200 mL of boiling water, boiling for 10 minutes, cooling to room temperature, adding 3.4 g of commercially available instant coffee and 2.5 g of mucin from porcine stomach (produced by Sigma-Aldrich Co. LLC) thereto, and uniformly stirring the mixture.

<Abrasive Ability (RDA Value)>

The RDA value was measured by the method of Hefferen et al. (J. Dent. Res., Vol. 55, No. 4, 563-573, 1976). This method is also described in detail in Japanese Unexamined Patent Publication No. S62-87507. Specifically, the measurement was performed as follows: 8 human teeth were provided in advance, and the dentine was irradiated with radioactive $^{32}$P (phosphorus-32), held using resin, and set in an 8-head abrasive machine under a brushing load of 150 g. Next, 40 mL of tap water was added to 25 g of the oral composition of each of the Examples and Comparative Examples, and well-mixed slurry was placed in each tank of the polishing machine and polished for 1,500 strokes. 3 mL of polished slurry was poured into a metal plate mold, and dried overnight while circulating the air at 60° C. The radioactivity of the surface of the thus-prepared dried slurry plate was measured. Using a dentine treated in the same manner as described above, slurry obtained by dissolving 100 g of calcium pyrophosphate in 50 mL of an aqueous solution of 0.5% carboxymethyl cellulose was measured in the same manner and regarded as a control example. Assuming the radiation dose in the control example to be 100, the value of each tank was calculated, and the average of 8 values was regarded as the RDA value.

The RDA value was used as an index of the abrasive ability. Hereinafter, the RDA value is regarded as the value of the abrasive ability.

Tables 2 to 5 summarize the results. The values described in the columns "Precipitated Silica" and "Fused Silica" indicate the amount (mass %) of these precipitated silica and fused silica added to each oral composition.

Further, Tables 2 to 5 also show the values of the ratio of stain removal ability to abrasive ability (stain removal ability/abrasive ability) of the oral composition of each Example. An oral composition whose removal ability is high relative to the abrasive ability (i.e., an oral composition having a greater ratio (stain removal ability/abrasive ability)) can be evaluated as a better oral composition.

TABLE 2

|  | Comparative Example 1 | Example 1-1 | Example 1-2 | Example 1-3 | Example 1-4 | Example 1-5 | Example 1-6 | Example 1-7 | Example 1-8 | Example 1-9 |
| --- | --- | --- | --- | --- | --- | --- | --- | --- | --- | --- |
| Precipitated silica | 17 | 17 | 17 | 17 | 17 | 17 | 17 | 17 | 17 | 17 |
| Fused silica | 0 | 0.5 | 2 | 2.5 | 3 | 3.5 | 4.5 | 6 | 8.5 | 10 |
| Stain removal ability | 20 | 25 | 27 | 32 | 32 | 35 | 36 | 30 | 30 | 27 |
| Abrasive ability | 103 | 103 | 103 | 114 | 109 | 110 | 120 | 132 | 132 | 132 |
| Stain removal ability/abrasive ability | 0.19 | 0.24 | 0.26 | 0.28 | 0.29 | 0.32 | 0.30 | 0.23 | 0.23 | 0.20 |

TABLE 3

|  | Comparative Example 2 | Example 2-1 | Example 2-2 | Example 2-3 | Example 2-4 | Example 2-5 | Example 2-6 | Example 2-7 | Example 2-8 |
| --- | --- | --- | --- | --- | --- | --- | --- | --- | --- |
| Precipitated silica | 0 | 5 | 7.5 | 15 | 17 | 20 | 22 | 24 | 26 |
| Fused silica | 3 | 3 | 3 | 3 | 3 | 3 | 3 | 3 | 3 |
| Stain removal ability | 20 | 24 | 25 | 27 | 32 | 35 | 41 | 33 | 30 |
| Abrasive ability | 89 | 100 | 98 | 109 | 109 | 120 | 130 | 140 | 130 |
| Stain removal ability/abrasive ability | 0.22 | 0.24 | 0.26 | 0.25 | 0.29 | 0.29 | 0.32 | 0.24 | 0.23 |

TABLE 4

|  | Example 3-1 | Example 3-2 | Example 3-3 | Example 3-4 | Example 3-5 | Example 3-6 |
| --- | --- | --- | --- | --- | --- | --- |
| Precipitated silica | 22 | 22 | 22 | 22 | 22 | 22 |
| Fused silica | 0.25 | 0.5 | 2.5 | 3 | 4.5 | 6.0 |
| Stain removal ability | 25 | 27 | 35 | 41 | 33 | 29 |
| Abrasive ability | 93 | 90 | 140 | 130 | 106 | 121 |
| Stain removal ability/abrasive ability | 0.27 | 0.30 | 0.25 | 0.32 | 0.31 | 0.24 |

TABLE 5

|  | Comparative Example 3 | Comparative Example 4 | Comparative Example 5 | Example 4 | Example 5 | Example 6 | Example 7 |
| --- | --- | --- | --- | --- | --- | --- | --- |
| Precipitated silica | 0 | 24 | 30 | 21.5 | 24 | 24 | 26 |
| Fused silica | 2.5 | 0 | 0 | 3.5 | 3.5 | 6.0 | 3.5 |
| Stain removal ability | 20 | 21 | 23 | 46 | 28 | 28 | 29 |
| Abrasive ability | 79 | 123 | 153 | 127 | 127 | 117 | 132 |
| Stain removal ability/abrasive ability | 0.25 | 0.17 | 0.15 | 0.36 | 0.22 | 0.24 | 0.22 |

As shown in Table 2, in the case where 17% by mass of precipitated silica was added to the total mass of the oral composition, the stain removal ability was 25 or greater when the fused silica was added thereto. In particular, when 0.5 to 8.5% by mass of the fused silica was added, the stain removal ability was 25 or greater, and the ratio of stain removal ability to abrasive ability (stain removal ability/abrasive ability) was about 0.23 or greater, thus indicating that a more preferable oral composition can be obtained.

Further, as shown in Table 3, in the case where 3% by mass of fused silica was added to the total mass of the oral composition, the stain removal ability was 24 or greater when the precipitated silica was added thereto. In particular, when 7.5 to 26% by mass of the precipitated silica was added, the stain removal ability was 25 or greater, and the ratio (stain removal ability/abrasive ability) was about 0.23 or greater, thus indicating that a more preferable oral composition can be obtained.

Additionally, as shown in Table 4, in the case where 22% by mass of fused silica was added to the total mass of the oral composition, the stain removal ability was 25 or greater when the precipitated silica was added thereto. Specifically, when at least 0.25 to 6% by mass of the fused silica was added, the stain removal ability was 25 or greater, and the ratio (stain removal ability/abrasive ability) was about 0.24 or greater, thus indicating that a preferable oral composition can be obtained.

Further, it became clear from all Comparative Examples that an oral composition whose stain removal ability is 24 or greater cannot be obtained when the oral composition was produced by adding only fused silica or precipitated silica.

Additionally, it became clear from all Examples, that an oral composition comprising fused silica and precipitated silica is preferable because at least the stain removal ability thereof is 24 or greater; an oral composition comprising 0.25 to 8.5% by mass (or 0.5 to 8.5% by mass) of fused silica and 5 to 26% by mass (or 7.5 to 26% by mass) of precipitated silica is more preferable because the stain removal ability thereof is 25 or greater, and the ratio (stain removal ability/ abrasive ability) is about 0.24 or greater; and an oral composition comprising 2 to 4.5% by mass of fused silica and 15 to 22% by mass of precipitated silica is still more preferable because the stain removal ability thereof is 27 or greater, and the ratio (stain removal ability/abrasive ability) is about 0.25 or greater.

In the tables, Example 1-4 and Example 2-4 are the same, and Example 2-6 and Example 3-4 are the same.

[Examination of the Elimination of Uncomfortable Sensation at the Time of Use]

The oral composition containing fused silica may leave a gritty, uncomfortable sensation in the oral cavity (uncomfortable sensation as if stones or sand is inside the oral cavity) when the oral composition is applied into the oral cavity (for example, placing the oral composition on a toothbrush to brush the teeth), as described above. Such a sensation may not be a problem to some users, but it is not very desirable. Therefore, a preferable particle size and amount of fused silica to be added to the oral composition were examined in view of the uncomfortable sensation.

<Examination of the Particle Size of Fused Silica>

This examination was performed using the fused silica used in the above-described examination of the abrasive ability and the stain removal ability. The fused silica was sieved through meshes of various sizes shown in Table 7, and silica particles having a large particle size were removed. Then, using fused silica obtained after the removal procedure, oral compositions (Reference Examples 1 to 4) were prepared in accordance with the composition shown in the prescription (Table 6) described below. The abrasive precipitated silica in the prescription below is the same precipitated silica used in the above-described examination of the abrasive ability and the stain removal ability. Further, the thickening precipitated silica in the prescription below has an oil absorption of 335 (mL/100 g) and a BET specific surface area of 236 (m$^2$/g).

TABLE 6

| Prescription: Composition of Reference Examples 1 to 4 | |
|---|---|
| Components | Amount (mass %) |
| Fused silica (mesh diameter is shown in Table 7) | 5.0 |
| Abrasive Precipitated silica | 13.0 |
| Thickening precipitated silica | 1.0 |
| Sorbitol | 24.0 |
| Glycerol | 5.0 |
| Polyethyleneglycol 400 | 5.0 |
| Xanthan gum | 0.5 |
| Carboxymethyl cellulose | 0.7 |
| Sodium lauryl sulfate | 1.2 |
| Flavoring | 1.0 |
| Sodium saccharin | 0.2 |
| Purified water | Balance |
| Total | 100 |

Subjects evaluated the sensation when they brushed their teeth by using an appropriate amount of each oral composition (Reference Examples 1 to 4) with the toothbrush. Specifically, 10 subjects brushed their teeth using each oral composition, and selected one out of the three following levels with respect to the question "how much of a gritty sensation did you feel?"

"I felt no such sensation at all." (3 points)

"I felt such a sensation, but it was not uncomfortable." (2 points)

"I felt an uncomfortable sensation." (1 point)

Consequently, the average point of 10 people was calculated. An average point of 2.5 or higher was evaluated as "I", an average point of 2 or more and less than 2.5 was evaluated as "II", and an average point of less than 2 was evaluated as "III". Table 7 also shows the results.

TABLE 7

| | Mesh size (μm) used to remove particles having a large particle size | Evaluation of the sensation |
|---|---|---|
| Reference Example 1 | 150 | III (average point: 1.5) |
| Reference Example 2 | 75 | II (average point: 2.3) |
| Reference Example 3 | 53 | I (average point: 2.7) |
| Reference Example 4 | 45 | I (average point: 2.9) |

It was found that there was no particular problem in the sensation when an oral composition containing fused silica in which particles of a large particle size were removed (i.e., fused silica was sieved) using a 75-μm mesh or smaller was used. It was also found that a good sensation can be obtained when an oral composition containing fused silica in which particles of a large particle size were removed (i.e., fused silica was sieved) using a 53-μm mesh or smaller.

<Examination of the Amount of Fused Silica>

Oral compositions of Reference Example 3.1, Reference Example 3.2, and Reference Example 3.3 were prepared in the same manner as in the preparation of the oral composition of Reference Example 3 above, except that the amount of silica was changed. Specifically, silica contained in these Reference Examples is fused silica in which particles having a large particle size were removed (i.e., sieved) using a 53-μm mesh. Table 8 shows the amount of silica (mass %) relative to the total mass of the composition in each Reference Example.

Further, the sensation was evaluated in the same manner described above. Table 8 also shows the results.

TABLE 8

|  | Amount of silica contained (mass %) | Evaluation of the sensation |
|---|---|---|
| Reference Example 3.3 | 15 | III (average point: 1.6) |
| Reference Example 3.2 | 10 | II (average point: 2.1) |
| Reference Example 3.1 | 7.5 | I (average point: 2.5) |
| Reference Example 3 | 5 | I (average point: 2.7) |

It was found that there was no particular problem in the sensation at least when the amount of fused silica contained was 10% by mass or less. It was also found that a good sensation can be obtained when the amount of fused silica contained was 7.5% by mass or less.

[Examination of the Combination of Different Types of Fused Silica Having Different Particle Sizes]

How the properties of the oral composition change by the use of two (or more) types of fused silica having different particle sizes in combination was examined.

The target oral composition of the examination was produced based on the composition described in Table 1, except that the amount (mass %) of precipitated silica and the amount (mass %) of fused silica were in accordance with the values described in Tables 9 and 10 below.

Fused silica used for the production of the oral composition is a mixture of fused silica (powder) having a relatively small average particle size and fused silica (powder) having a relatively large average particle size. Hereafter, the former is also referred to as fine fused silica, and the latter is also referred to as coarse fused silica.

The average particle size herein is a median diameter (d50), and is the value measured using a laser diffraction scattering measuring device (LA-920, produced by Horiba, Ltd.). The average particle size of fine fused silica is 3.1 μm, and the distribution range thereof is 0.1 to 10 μm. The average particle size of coarse fused silica is 17.4 μm, and the distribution range thereof is 10 to 45 μm. Tables 9 and 10 also show the amount (mass %) of fine fused silica and coarse fused silica contained in the oral composition.

The stain removal ability, the abrasive ability, and the ratio (stain removal ability/abrasive ability) of each oral composition produced were measured in the same manner described in "Examination of Abrasive Ability and Stain Removal Ability" above. Tables 9 and 10 also show these results.

TABLE 9

|  |  | Example A-1 | Example A-2 | Example A-3 | Example A-4 | Example A-5 |
|---|---|---|---|---|---|---|
| Precipitated silica |  | 22 | 22 | 22 | 22 | 22 |
| Fused silica | Amount | 3 | 3 | 3 | 3 | 3 |
|  | Fine powder (3.1 μm) | 0 | 0.3 | 0.9 | 2.7 | 3 |
|  | Coarse powder (17.4 μm) | 3 | 2.7 | 2.1 | 0.3 | 0 |
| Stain removal ability |  | 29 | 34 | 41 | 42 | 36 |
| Abrasive ability |  | 110 | 120 | 130 | 141 | 135 |
| Stain removal ability/abrasive ability |  | 0.26 | 0.29 | 0.32 | 0.30 | 0.27 |

TABLE 10

|  |  | Example B-1 | Example B-2 | Example B-3 |
|---|---|---|---|---|
| Precipitated silica |  | 17 | 17 | 17 |
| Fused silica | Amount | 3 | 3 | 3 |
|  | Fine powder (3.1 μm) | 0.9 | 2.4 | 2.7 |
|  | Coarse powder (17.4 μm) | 2.1 | 0.6 | 0.3 |
| Stain removal ability |  | 32 | 36 | 39 |
| Abrasive ability |  | 109 | 115 | 130 |
| Stain removal ability/abrasive ability |  | 0.29 | 0.31 | 0.30 |

In the production of each oral composition, the percentages of fine fused silica relative to the total fused silica used in Examples A-1, A-2, A-3, A-4, and A-5 were 0, 10, 30, 90, and 100%, respectively. The percentages thereof in Examples B-1, B-2, and B-3 were 30, 80, and 90%, respectively.

It was found from Tables 9 and 10 that the stain removal ability was greater and the ratio (stain removal ability/abrasive ability) was higher when fine fused silica and coarse fused silica were used in combination, than when used singly. Specifically, it was found to be more preferable when 30 to 90% of fine fused silica was contained in the total fused silica used, because the stain removal ability was even greater and the ratio (stain removal ability/abrasive ability) was increased.

Prescription examples of the oral composition of the present invention are shown below. The amount (%) in each prescription example indicates mass %. In the following prescription examples, 7 types of fused silica (fused silica A to G) are used, and all of these are fused silica (thermally sprayed and fused silica) produced by a spraying method. The mesh size for sieving fused silica A to G, the degree of roundness, the BET specific surface area, and the oil absorption (linseed oil absorption; JIS K5101) are as follows.

Fused silica A: mesh size of 60 (μm), degree of roundness of 0.90, BET specific surface area of 10.0 ($m^2$/g), and oil absorption of 9.8 (mL/100 g)

Fused silica B: mesh size of 55 (μm), degree of roundness of 0.93, BET specific surface area of 8.0 ($m^2$/g), and oil absorption of 7.7 of (mL/100 g)

Fused silica C: mesh size of 53 (μm), degree of roundness of 0.95, BET specific surface area of 5.0 ($m^2$/g), and oil absorption of 3.5 (mL/100 g)

Fused silica D: mesh size of 45 (μm), degree of roundness of 0.98, BET specific surface area of 4.6 (m$^2$/g), and oil absorption of 3.2 (mL/100 g)

Fused silica E: mesh size of 60 (μm), degree of roundness of 0.94, BET specific surface area of 6.0 (m$^2$/g), and oil absorption 5.5 (mL/100 g)

Fused silica F: mesh size of 55 (μm), degree of roundness of 0.97, BET specific surface area of 4.8 (m$^2$/g), and oil absorption of 3.3 (mL/100 g)

Fused silica G: mesh size of 53 (μm), degree of roundness of 0.91, BET specific surface area of 9.1 (m$^2$/g), and oil absorption of 8.3 (mL/100 g)

TABLE 11

<Prescription Example 1> Dentifrice

| Components | Amount (%) |
|---|---|
| Fused silica A | 2.0 |
| Crystalline cellulose | 18.0 |
| Thickening precipitated silica | 5.0 |
| Sorbitol | 40.0 |
| Xanthan gum | 0.6 |
| Sodium pyrophosphate | 3.0 |
| Sodium phosphate | 0.5 |
| Sodium hydrogen phosphate | 0.2 |
| Sodium fluoride | 0.2 |
| Triclosan | 0.1 |
| Titanium oxide | 0.5 |
| Sodium lauryl sulfate | 1.0 |
| Flavoring | 1.0 |
| Sodium saccharin | 0.2 |
| Purified Water | Balance |
| Total | 100.0 |

TABLE 12

<Prescription Example 2> Dentifrice

| Components | Amount (%) |
|---|---|
| Fused silica B | 4.5 |
| Calcium hydrogen phosphate | 13.0 |
| Xanthan gum | 0.6 |
| Sodium polyacrylate | 0.3 |
| Sodium monofluorophosphate | 0.7 |
| Potassium nitrate | 5.0 |
| Tocopherol nicotinate | 0.05 |
| Glyceryl monostearate | 1.2 |
| Flavoring | 1.0 |
| Sodium saccharin | 0.2 |
| Reduced palatinose | 5.0 |
| Purified Water | Balance |
| Total | 100.0 |

TABLE 13

<Prescription Example 3> Dentifrice

| Components | Amount (%) |
|---|---|
| Fused silica C | 6.0 |
| Calcium carbonate | 15.0 |
| Thickening precipitated silica | 6.0 |
| Glycerol | 10.0 |
| Xanthan gum | 0.7 |
| Sodium carboxymethyl cellulose | 0.5 |
| Sodium polyacrylate | 0.4 |
| Sodium monofluorophosphate | 0.7 |
| Tocopherol acetate | 0.1 |
| Sodium lauroyl sarcosine | 0.1 |

TABLE 13-continued

<Prescription Example 3> Dentifrice

| Components | Amount (%) |
|---|---|
| Sodium lauryl sulfate | 1.0 |
| Methylparaben | 0.1 |
| Flavoring | 1.0 |
| Sodium saccharin | 0.2 |
| Purified Water | Balance |
| Total | 100.0 |

TABLE 14

<Prescription Example 4> Dentifrice

| Components | Amount (%) |
|---|---|
| Fused silica D | 7.5 |
| Aluminium hydroxide | 20.0 |
| Thickening precipitated silica | 8.0 |
| Glycerol | 20.0 |
| Sodium carboxymethyl cellulose | 0.7 |
| Sodium monofluorophosphate | 0.7 |
| Dipotassium glycyrrhizinate | 0.02 |
| Polyoxyethylene (60) hydrogenated castor oil | 1.0 |
| Alkyl (8-16) glucoside | 1.0 |
| Flavoring | 1.0 |
| Sodium saccharin | 0.05 |
| L-Menthol | 0.5 |
| Purified Water | Balance |
| Total | 100.0 |

TABLE 15

<Prescription Example 5> Dentifrice

| Components | Amount (%) |
|---|---|
| Fused silica E | 8.5 |
| Thickening precipitated silica | 6.0 |
| Glycerol | 20.0 |
| Hydroxyethyl cellulose | 0.7 |
| Carrageenan | 0.3 |
| Sodium alginate | 0.7 |
| Sodium monofluorophosphate | 0.7 |
| Dipotassium glycyrrhizinate | 0.02 |
| Polyoxyethylene (60) hydrogenated castor oil | 1.0 |
| Alkyl (8-16) glucoside | 1.5 |
| Flavoring | 1.0 |
| Sodium saccharin | 0.05 |
| Reduced palatinose | 10.0 |
| Purified Water | Balance |
| Total | 100.0 |

TABLE 16

<Prescription Example 6> Dentifrice

| Components | Amount (%) |
|---|---|
| Fused silica F | 0.5 |
| Abrasive precipitated silica | 18.0 |
| Polyethylene powder | 3.0 |
| Sorbitol | 20.0 |
| Glycerol | 8.0 |
| Polyethyleneglycol 200 | 3.0 |
| Xanthan gum | 0.7 |
| Sodium carboxymethyl cellulose | 0.7 |
| Sodium hydroxide | 1.0 |
| Erythritol | 0.5 |

TABLE 16-continued

<Prescription Example 6> Dentifrice

| Components | Amount (%) |
| --- | --- |
| Tocopherol acetate | 0.1 |
| Triclosan | 0.1 |
| Propylene glycol monostearate | 1.0 |
| Titanium oxide | 0.5 |
| Flavoring | 1.0 |
| Sodium saccharin | 0.2 |
| L-Menthol | 0.5 |
| Purified Water | Balance |
| Total | 100.0 |

TABLE 17

<Prescription Example 7> Dentifrice

| Components | Amount (%) |
| --- | --- |
| Fused silica G | 0.5 |
| Abrasive silica gel | 18.0 |
| Silylated precipitated silica | 2.0 |
| Sorbitol | 25.0 |
| Polyethyleneglycol 600 | 3.0 |
| Xanthan gum | 0.7 |
| Sodium carboxymethyl cellulose | 0.7 |
| Sodium hydroxide | 1.0 |
| Phytic acid | 0.5 |
| Tocopherol acetate | 0.1 |
| Triclosan | 0.1 |
| Sodium lauryl sulfate | 1.0 |
| Titanium oxide | 0.5 |
| Flavoring | 1.0 |
| Sodium saccharin | 0.2 |
| L-Menthol | 0.5 |
| Purified Water | Balance |
| Total | 100.0 |

TABLE 18

<Prescription Example 8> Dentifrice

| Components | Amount (%) |
| --- | --- |
| Fused silica A | 7.5 |
| Abrasive precipitated silica | 5.0 |
| Calcium hydrogen phosphate for toothpaste | 10.0 |
| Glycerol | 8.0 |
| Polyethyleneglycol 1000 | 3.0 |
| Sodium carboxymethyl cellulose | 0.7 |
| Magnesium phosphate | 0.5 |
| Hydroxyapatite | 2.0 |
| Sodium lauroyl sarcosine | 1.0 |
| Zeolite | 0.5 |
| Glyceryl monostearate | 1.2 |
| Flavoring | 1.0 |
| Sodium saccharin | 0.2 |
| Purified Water | Balance |
| Total | 100.0 |

TABLE 19

<Prescription Example 9> Dentifrice

| Components | Amount (%) |
| --- | --- |
| Fused silica B | 1.0 |
| Abrasive precipitated silica | 18.0 |
| Cellulose powder | 5.0 |

TABLE 19-continued

<Prescription Example 9> Dentifrice

| Components | Amount (%) |
| --- | --- |
| Sorbitol | 20.0 |
| Polyethyleneglycol 1500 | 3.0 |
| Carrageenan | 0.7 |
| Glycerol fatty acid ester | 1.0 |
| Potassium hydroxide solution | 1.0 |
| DL-malic acid | 0.5 |
| Sodium fluoride | 0.2 |
| Sodium lauryl sulfate | 1.0 |
| Titanium oxide | 0.5 |
| Flavoring | 1.0 |
| Sodium saccharin | 0.2 |
| L-Menthol | 0.5 |
| Purified Water | Balance |
| Total | 100.0 |

TABLE 20

<Prescription Example 10> Dentifrice

| Components | Amount (%) |
| --- | --- |
| Fused silica A | 5.0 |
| Fused silica C | 3.0 |
| Sorbitol | 20.0 |
| Polyethyleneglycol 2000 | 3.0 |
| Sodium fluoride | 0.2 |
| Sodium lauryl sulfate | 1.0 |
| Titanium oxide | 0.5 |
| Mica | 1.0 |
| Flavoring | 1.0 |
| Sodium saccharin | 0.2 |
| Mint oil | 0.5 |
| Purified Water | Balance |
| Total | 100.0 |

TABLE 21

<Prescription Example 11> Dentifrice

| Components | Amount (%) |
| --- | --- |
| Fused silica D | 6.5 |
| Abrasive precipitated silica | 8.0 |
| Tricalcium phosphate | 5.0 |
| Calcium hydrogen phosphate | 10.0 |
| Sorbitol | 20.0 |
| Ethanol | 5.0 |
| Polyethyleneglycol 400 | 3.0 |
| Magnesium phosphate | 0.5 |
| Sodium carboxymethyl cellulose | 0.7 |
| Sodium monofluorophosphate | 0.7 |
| Zeolite | 0.5 |
| ε-aminocaproic acid | 0.1 |
| Sodium lauryl sulfate | 1.0 |
| Paraben | 0.1 |
| Flavoring | 1.0 |
| Xylitol | 0.2 |
| L-Menthol | 0.5 |
| Purified Water | Balance |
| Total | 100.0 |

TABLE 22

<Prescription Example 12> Dentifrice

| Components | Amount (%) |
|---|---|
| Fused silica E | 3.0 |
| Abrasive precipitated silica | 18.0 |
| Thickening precipitated silica | 1.0 |
| Sorbitol | 20.0 |
| Glycerol | 8.0 |
| Propylene glycol | 5.0 |
| Polyethyleneglycol 4000 | 3.0 |
| Sodium carboxymethyl cellulose | 0.7 |
| Sodium fluoride | 0.2 |
| Isopropylmethylphenol | 0.05 |
| Sodium lauryl sulfate | 1.0 |
| Polyoxyethylene (2 mol) Alkyl (12-14) disodium sulfosuccinate | 1.0 |
| Polyoxyethylene (60) hydrogenated castor oil | 0.5 |
| Titanium oxide | 1.0 |
| Flavoring | 0.2 |
| Sodium saccharin | 0.1 |
| Stevia extract | |
| Purified Water | Balance |
| Total | 100.0 |

TABLE 23

<Prescription Example 13> Dentifrice

| Components | Amount (%) |
|---|---|
| Fused silica F | 2.5 |
| Thickening precipitated silica | 3.0 |
| Sorbitol | 20.0 |
| Propylene glycol | 8.0 |
| Xanthan gum | 0.7 |
| Sodium hydrogen carbonate | 0.5 |
| Sodium monofluorophosphate | 0.7 |
| Sodium lauroyl sarcosine | 1.0 |
| Dextranase | 0.5 |
| Sodium lauryl sulfate | 1.0 |
| Paraben | 0.1 |
| DL-Alanine | 0.5 |
| Flavoring | 1.0 |
| Sodium saccharin | 0.2 |
| L-Menthol | 0.5 |
| Purified Water | Balance |
| Total | 100.0 |

TABLE 24

<Prescription Example 14> Dentifrice

| Components | Amount (%) |
|---|---|
| Fused silica G | 2.5 |
| Aluminium hydroxide | 8.0 |
| Thickening precipitated silica | 3.0 |
| Sorbitol | 20.0 |
| Propylene glycol | 8.0 |
| Xanthan gum | 0.7 |
| 2-Alkyl N-hydroxyethylimidazolinium betain | 0.5 |
| Sodium hydrogen carbonate | 0.5 |
| Sodium monofluorophosphate | 0.7 |
| Sodium lauroyl sarcosine | 1.0 |
| Dextranase | 0.5 |
| Sodium lauryl sulfate | 1.0 |
| Paraben | 0.1 |
| Titanium oxide | 0.5 |
| Flavoring | 1.0 |

TABLE 24-continued

<Prescription Example 14> Dentifrice

| Components | Amount (%) |
|---|---|
| Sodium saccharin | 0.2 |
| L-Menthol | 0.5 |
| Purified Water | Balance |
| Total | 100.0 |

TABLE 25

<Prescription Example 15> Dentifrice

| Components | Amount (%) |
|---|---|
| Fused silica A | 8.0 |
| Abrasive silica gel | 5.0 |
| Sorbitol | 20.0 |
| Xanthan gum | 0.7 |
| Sodium polyphosphate | 0.7 |
| Sodium alginate | 0.7 |
| Sodium fluoride | 0.2 |
| Sodium lauroyl sarcosine | 1.0 |
| Hydroxyethyl cellulose dimethyl diallyl ammonium chloride | 0.2 |
|  | 0.1 |
| Benzalkonium chloride | 0.5 |
| Sodium lauryl sulfate | 1.0 |
| Polyoxyethylene (60) hydrogenated castor oil | 0.5 |
| Titanium oxide | 1.0 |
| Flavoring | 0.2 |
| Xylitol | 0.5 |
| L-Menthol | |
| Purified Water | Balance |
| Total | 100.0 |

TABLE 26

<Prescription Example 16> Dentifrice

| Components | Amount (%) |
|---|---|
| Fused silica B | 1.5 |
| Abrasive precipitated silica | 20.0 |
| Thickening fumed silica | 5.0 |
| Sorbitol | 20.0 |
| Propylene glycol | 8.0 |
| Polyethyleneglycol 6000 | 3.0 |
| Xanthan gum | 0.7 |
| Sodium fluoride | 0.2 |
| Isopropylmethylphenol | 0.05 |
| ε-aminocaproic acid | 0.1 |
| Sodium lauryl sulfate | 1.0 |
| Titanium oxide | 0.5 |
| Flavoring | 1.0 |
| Sodium saccharin | 0.2 |
| L-Menthol | 0.5 |
| Purified Water | Balance |
| Total | 100.0 |

TABLE 27

<Prescription Example 17> Dentifrice

| Components | Amount (%) |
|---|---|
| Fused silica C | 4.0 |
| Calcium carbonate | 15.0 |
| Abrasive precipitated silica | 5.0 |
| Sorbitol | 20.0 |
| Glycerol | 5.0 |

TABLE 27-continued

<Prescription Example 17> Dentifrice

| Components | Amount (%) |
| --- | --- |
| Sodium carboxymethyl cellulose | 0.7 |
| Polyoxyethylene sorbitan monostearate | 0.5 |
| Sodium hydroxide | 0.5 |
| Sodium chloride | 15.0 |
| Sodium monofluorophosphate | 0.7 |
| β-glycyrrhetinate | 0.02 |
| Sodium lauryl sulfate | 1.0 |
| Titanium oxide | 0.5 |
| Flavoring | 1.0 |
| Sodium saccharin | 0.2 |
| Purified Water | Balance |
| Total | 100.0 |

TABLE 28

<Prescription Example 18> Dentifrice

| Components | Amount (%) |
| --- | --- |
| Fused silica D | 4.0 |
| Abrasive precipitated silica | 10.0 |
| Sorbitol | 20.0 |
| Carrageenan | 0.7 |
| Sodium carboxymethyl cellulose | 0.7 |
| Sodium N-lauroyl-L-glutamate | 0.5 |
| Sodium hydrogen carbonate | 0.007 |
| Sodium chloride | 10.0 |
| Sodium monofluorophosphate | 0.7 |
| Benzethonium chloride | 0.1 |
| Sodium lauryl sulfate | 1.0 |
| Titanium oxide | 0.5 |
| Flavoring | 1.0 |
| Sodium saccharin | 0.2 |
| Purified Water | Balance |
| Total | 100.0 |

TABLE 29

<Prescription Example 19> Dentifrice

| Components | Amount (%) |
| --- | --- |
| Fused silica E | 5.5 |
| Silica gel | 10.0 |
| Calcium carbonate | 5.0 |
| Zinc oxide | 1.0 |
| Sorbitol | 20.0 |
| Polyethyleneglycol 11000 | 3.0 |
| Sodium carboxymethyl cellulose | 0.7 |
| Sodium monofluorophosphate | 0.7 |
| Benzethonium chloride | 0.1 |
| Sodium lauryl sulfate | 1.0 |
| Flavoring | 1.0 |
| Sodium saccharin | 0.2 |
| Purified Water | Balance |
| Total | 100.0 |

TABLE 30

<Prescription Example 20> Dentifrice

| Components | Amount (%) |
| --- | --- |
| Fused silica F | 3.5 |
| Abrasive precipitated silica | 15.0 |
| Zinc oxide | 1.0 |

TABLE 30-continued

<Prescription Example 20> Dentifrice

| Components | Amount (%) |
| --- | --- |
| Sorbitol | 20.0 |
| Glycerol | 5.0 |
| Polyethyleneglycol 20000 | 3.0 |
| Polyethylene powder | 0.5 |
| Xanthan gum | 0.7 |
| Sodium carboxymethyl cellulose | 0.7 |
| Cocamidopropyl betaine | 0.5 |
| Sodium hydroxide | 0.5 |
| Sodium tripolyphosphate | 0.3 |
| Sodium pyrophosphate | 0.2 |
| Sodium monofluorophosphate | 0.7 |
| Sodium lauryl sulfate | 1.0 |
| Titanium oxide | 0.5 |
| Flavoring | 1.0 |
| Sodium saccharin | 0.2 |
| Purified Water | Balance |
| Total | 100.0 |

TABLE 31

<Prescription Example 21> Dentifrice

| Components | Amount (%) |
| --- | --- |
| Fused silica G | 3.5 |
| Abrasive precipitated silica | 15.0 |
| Sorbitol | 20.0 |
| Propylene glycol | 3.0 |
| Carrageenan | 0.7 |
| Sodium carboxymethyl cellulose | 0.7 |
| Sodium hydroxide | 0.5 |
| Methylvinylether/maleic acid copolymer | 0.5 |
| Sodium fluoride | 0.2 |
| Triclosan | 0.1 |
| Sodium lauryl sulfate | 1.0 |
| Titanium oxide | 0.5 |
| Flavoring | 1.0 |
| Sodium saccharin | 0.2 |
| Purified Water | Balance |
| Total | 100.0 |

TABLE 32

<Prescription Example 22> Dentifrice

| Components | Amount (%) |
| --- | --- |
| Fused silica A | 3.5 |
| Silica gel | 15.0 |
| Sorbitol | 10.0 |
| Glycerol | 5.0 |
| Polyethyleneglycol 300 | 5.0 |
| Xanthan gum | 0.7 |
| Sodium carboxymethyl cellulose | 0.7 |
| Sodium hydroxide | 0.5 |
| Sodium metaphosphate | 0.5 |
| Cocamidopropyl betaine | 0.3 |
| Carbomer 956 | 0.3 |
| Poloxamer 407 | 0.2 |
| Sodium monofluorophosphate | 0.7 |
| Sodium lauryl sulfate | 1.0 |
| Titanium oxide | 0.5 |
| Flavoring | 1.0 |
| Sodium saccharin | 0.2 |
| Purified Water | Balance |
| Total | 100.0 |

TABLE 33

<Prescription Example 23> Dentifrice

| Components | Amount (%) |
|---|---|
| Fused silica B | 3.5 |
| Abrasive precipitated silica | 15.0 |
| Sorbitol | 10.0 |
| Polyethyleneglycol 1540 | 5.0 |
| Xanthan gum | 1.0 |
| Sodium monohydrogen phosphate (anhydrous) | 0.5 |
| Sodium benzoate | 0.5 |
|  | 0.5 |
| Sodium fluoride | 0.2 |
| Sodium polyoxyethylene lauryl ether sulfate | 1.0 |
| Titanium oxide | 0.5 |
| Mica | 0.2 |
| Flavoring | 1.0 |
| Sodium saccharin | 0.2 |
| Purified Water | Balance |
| Total | 100.0 |

TABLE 34

<Prescription Example 24> Dentifrice

| Components | Amount (%) |
|---|---|
| Fused silica C | 3.5 |
| Abrasive silica gel | 15.0 |
| Sorbitol | 10.0 |
| Glycerol | 5.0 |
| Polyethyleneglycol 400 | 5.0 |
| Sodium carboxymethyl cellulose | 0.7 |
| Sodium monohydrogen phosphate (anhydrous) | 1.0 |
| Lecithin | 0.5 |
| Methylvinylether/maleic acid copolymer | 0.5 |
| Sodium fluoride | 0.2 |
| Sodium lauryl sulfate | 1.0 |
| Mica | 0.2 |
| Flavoring | 1.0 |
| Sodium saccharin | 0.2 |
| Limonene | 0.5 |
| Purified Water | Balance |
| Total | 100.0 |

TABLE 35

<Prescription Example 25> Dentifrice

| Components | Amount (%) |
|---|---|
| Fused silica D | 3.5 |
| Abrasive precipitated silica | 15.0 |
| Glycerol | 5.0 |
| Propylene glycol | 5.0 |
| Polyethyleneglycol 400 | 5.0 |
| Xanthan gum | 0.7 |
| Sodium carboxymethyl cellulose | 0.7 |
| Calcium peroxide | 1.0 |
| Sodium hydrogen carbonate | 0.5 |
| Sodium hydroxide | 0.5 |
| Poloxamer 407 | 0.3 |
| Potassium pyrophosphate | 0.2 |
| Sodium monofluorophosphate | 0.7 |
| Sodium lauryl sulfate | 1.0 |
| Titanium oxide | 0.5 |
| Flavoring | 1.0 |
| Sodium saccharin | 0.2 |
| Purified Water | Balance |
| Total | 100.0 |

TABLE 36

<Prescription Example 26> Dentifrice

| Components | Amount (%) |
|---|---|
| Fused silica E | 3.5 |
| Abrasive precipitated silica | 15.0 |
| Glycerol | 5.0 |
| Polyethyleneglycol 4000 | 5.0 |
| Carrageenan | 0.7 |
| Polyvinylpyrrolidone | 0.5 |
| Sodium polyphosphate | 0.7 |
| Hydroxyethyl cellulose dimethyl diallyl ammonium chloride | 0.2 0.7 |
| Sodium monofluorophosphate | 1.0 |
| Sodium lauryl sulfate | 0.5 |
| Polyoxyethylene (60) hydrogenated castor oil | 0.5 |
| Titanium oxide | 1.0 |
| Flavoring | 0.2 |
| Sodium saccharin |  |
| Purified Water | Balance |
| Total | 100.0 |

TABLE 37

<Prescription Example 27> Dentifrice

| Components | Amount (%) |
|---|---|
| Fused silica F | 3.5 |
| Abrasive precipitated silica | 15.0 |
| Glycerol | 5.0 |
| Polyethyleneglycol 4000 | 5.0 |
| Carrageenan | 0.7 |
| Polyvinylpyrrolidone | 0.5 |
| Sodium polyphosphate | 0.7 |
| Sodium monofluorophosphate | 0.7 |
| Sodium lauryl sulfate | 1.0 |
| Coconut oil fatty acid amide propyl betaine | 1.0 |
| Polyoxyethylene (60) hydrogenated castor oil | 0.5 |
| Polyoxyethylene stearyl ether | 0.5 |
| Titanium oxide | 0.5 |
| Flavoring | 2.0 |
| Sodium saccharin | 0.2 |
| Anhydrous caffeine | 0.1 |
| Purified Water | Balance |
| Total | 100.0 |

TABLE 38

<Prescription Example 28> Dentifrice

| Components | Amount (%) |
|---|---|
| Fused silica G | 3.5 |
| Calcium carbonate | 5.0 |
| Abrasive precipitated silica | 15.0 |
| Glycerol | 5.0 |
| Propylene glycol | 5.0 |
| Polyethyleneglycol 1540 | 5.0 |
| Agar powder | 1.0 |
| Sodium carboxymethyl cellulose | 0.7 |
| Hydrogen peroxide | 0.5 |
| Sodium monofluorophosphate | 0.7 |
| Benzethonium chloride | 0.5 |
| N-stearoyl-N-methyltaurine sodium | 0.5 |
| Sodium lauryl sulfate | 1.0 |
| Titanium oxide | 0.5 |
| Flavoring | 1.0 |
| Sodium saccharin | 0.2 |
| Purified Water | Balance |
| Total | 100.0 |

The invention claimed is:

1. An oral composition comprising:
   fused silica in an amount of 2 to 4.5% by mass; and precipitated silica in an amount of 15 to 22% by mass.

2. The oral composition according to claim 1, wherein the BET specific surface area of the fused silica is 10 m²/g or less.

3. The oral composition according to claim 1; Wherein the fused silica has an oil absorption of 20 mL/100 g or less.

4. The oral composition according to claim 1, wherein the mass ratio of the precipitated silica to fused silica (precipitated silica/fused silica) contained in the oral composition is 2.5-11:1.

5. The oral composition according to claim 1 for the use in the removal of stains attached to the teeth.

6. The oral composition according to claim 1, wherein the fused silica is fused silica in which particles having a particle size greater than 60 μm are removed by using a sizing device.

7. The oral composition according to claim 1, wherein the fused silica is fused silica sieved through a 60-μm mesh.

8. The oral composition according to claim 1, wherein the RDA value is 90 to 140.

9. The oral composition according to claim 1, wherein the fused silica is a mixture of a first fused silica having an average particle size of 0.1 to 10 μm and a second fused silica having an average particle size greater than 10 μm and is equal to or less than 45 μm, and wherein the mass of the first fused silica accounts for 10 to 90% of the total mass of the fused silica.

10. The oral composition according to claim 1, wherein the mass ratio of the precipitated silica to fused silica, (precipitated silica/fused silica) contained in the oral composition is from 3:1 to 8:1.

11. An oral composition having a stain removal ability of greater than 27 and a stain removal/abrasive ability ratio of 0.25 or more, and comprising:
    fused silica in an amount of 0.25 to 8.5% by mass; and
    precipitated silica in an amount of 5 to 26% by mass,
    wherein the stain removal ability ($\Delta E$) of greater than 27 is evaluated by measuring a surface color of a tooth surface using a L*a*b* color system using L*, a*, and b* values of the color of the tooth surface and based on formulas as follows:

$\Delta E = 100 \times (\Delta E1/\Delta E0)$, wherein $\Delta E1 = \sqrt{(L2-L1)^2 + (a2-a1)^2 + (b2-b1)^2}$ $\Delta E0 = \sqrt{(L2-L0)^2 + (a2-a0)^2 + (b2-b0)^2}$ L0, a0, and b0 respectively correspond to the L*, a*, and b* values of the surface color of the tooth surface before staining; and L1, a1, and b1 correspond to the L*, a*, and b* values of the surface color of the tooth surface after staining, and L2, a2, and b2 correspond to the surface color of the tooth surface after stain removal, abrasive ability of the oral composition is measured as a relative dentine abrasivity (RDA) value, and the stain removal/abrasive ability ratio ($\Delta E$/RDA) is 0.25 or more.

12. The oral composition according to claim 11, wherein the fused silica is contained in an amount of 2 to 4.5% by mass; and the precipitated silica is contained in an amount of 15 to 22% by mass.

13. The oral composition according to claim 11, wherein the BET specific surface area of the fused silica is 10 m²/g or less.

14. The oral composition according to claim 11, wherein the fused silica has an oil absorption of 20 mL/100 g or less.

15. The oral composition according to claim 12, wherein the fused silica has an oil absorption of 20 mL/100 g or less.

16. The oral composition according to claim 11, wherein the mass ratio of the precipitated silica to fused silica (precipitated silica/fused silica) contained in the oral composition is 2.5-11:1.

17. The oral composition according to claim 11, wherein the fused silica is fused silica sieved through a 60-μm mesh.

18. The oral composition according to claim 11, wherein the RDA value is 90 to 140.

19. The oral composition according to claim 11, wherein the fused silica is a mixture of a first fused silica having an average particle size of 0.1 to 10 μm and a second fused silica having an average particle size greater than 10 μm and is equal to or less than 45 μm, and wherein the mass of the first fused silica accounts for 10 to 90% of the total mass of the fused silica.

20. The oral composition according to claim 11, wherein the mass ratio of the precipitated silica to fused silica (precipitated silica/fused silica) contained in the oral composition is from 3:1 to 8:1.

* * * * *

UNITED STATES PATENT AND TRADEMARK OFFICE
CERTIFICATE OF CORRECTION

PATENT NO. : 9,186,308 B2
APPLICATION NO. : 14/211545
DATED : November 17, 2015
INVENTOR(S) : Hiroshi Sakamoto It is certified that error appears in the above-identified patent and that said Letters Patent is hereby corrected as shown below:

Correct name of applicant in item (71) on the Title page of the patent to read as follows:

SUNSTAR INC., Takatsuki-shi, Osaka (JP)

Signed and Sealed this
Third Day of May, 2016

Michelle K. Lee
*Director of the United States Patent and Trademark Office*